United States Patent
Bache et al.

(10) Patent No.: US 11,290,182 B2
(45) Date of Patent: Mar. 29, 2022

(54) METHODS AND DEVICES FOR COMMUNICATION OF DATA BETWEEN ELECTRONIC VAPING DEVICE AND EXTERNAL DEVICE

(71) Applicant: Altria Client Services LLC, Richmond, VA (US)

(72) Inventors: Terrance Theodore Bache, Richmond, VA (US); Dave Schiff, Richmond, VA (US); Chris Phelan, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 409 days.

(21) Appl. No.: 15/911,940

(22) Filed: Mar. 5, 2018

(65) Prior Publication Data

US 2019/0269175 A1 Sep. 5, 2019

(51) Int. Cl.
| | |
|---|---|
| *A24F 47/00* | (2020.01) |
| *H04B 10/114* | (2013.01) |
| *H04B 10/116* | (2013.01) |
| *H04B 10/50* | (2013.01) |
| *A24F 40/95* | (2020.01) |
| *A24F 15/01* | (2020.01) |
| *A24F 40/50* | (2020.01) |

(Continued)

(52) U.S. Cl.
CPC .......... *H04B 10/1141* (2013.01); *A24F 15/01* (2020.01); *A24F 40/50* (2020.01); *A24F 40/65* (2020.01); *A24F 40/95* (2020.01); *H04B 10/116* (2013.01); *H04B 10/502* (2013.01); *A24F 40/10* (2020.01); *A61M 2205/8206* (2013.01)

(58) Field of Classification Search
None
See application file for complete search history.

(56) References Cited

U.S. PATENT DOCUMENTS

| | | | |
|---|---|---|---|
| 7,100,420 | B2 | 9/2006 | Read et al. |
| 8,757,147 | B2 | 6/2014 | Terry et al. |
| 9,018,899 | B2 | 4/2015 | Xiang |

(Continued)

FOREIGN PATENT DOCUMENTS

| | | |
|---|---|---|
| WO | WO-2015/063126 A1 | 5/2015 |
| WO | WO-2015/127429 A1 | 8/2015 |

OTHER PUBLICATIONS

International Search Report and Written Opinion dated Jun. 3, 2019 in International Application No. PCT/EP2019/055456.

(Continued)

*Primary Examiner* — Michael J Felton
*Assistant Examiner* — Katherine A Will
(74) *Attorney, Agent, or Firm* — Harness, Dickey & Pierce, P.L.C.

(57) ABSTRACT

An embodiment of an electronic vaping device includes: a memory; a light emitting device configured to optically transmit information associated with the electronic vaping device to an external device; and processing circuitry coupled to the memory and the light emitting device. The processing circuitry may be configured to: collect the information associated with the electronic vaping device; store the information in the memory; detect a triggering event; and initiate optical transmission of the information by the light emitting device in response to detecting the triggering event.

36 Claims, 9 Drawing Sheets

(51) Int. Cl.
*A24F 40/65* (2020.01)
*A24F 40/10* (2020.01)

(56) References Cited

U.S. PATENT DOCUMENTS

| | | |
|---|---|---|
| 9,072,321 B2 | 7/2015 | Liu |
| 9,289,014 B2 | 3/2016 | Tucker et al. |
| 10,420,374 B2 | 9/2019 | Liu |
| 2006/0099554 A1 | 5/2006 | Frost |
| 2013/0192623 A1 | 8/2013 | Tucker et al. |
| 2013/0340775 A1 | 12/2013 | Juster et al. |
| 2013/0341218 A1 | 12/2013 | Liu |
| 2014/0053856 A1 | 2/2014 | Liu |
| 2014/0278258 A1 | 9/2014 | Shafer |
| 2014/0305820 A1 | 10/2014 | Xiang |
| 2015/0097513 A1 | 4/2015 | Liberti et al. |
| 2015/0128976 A1 | 5/2015 | Verleur et al. |
| 2015/0224268 A1 | 8/2015 | Henry et al. |
| 2015/0333552 A1 | 11/2015 | Alarcon |
| 2016/0204637 A1 | 7/2016 | Alarcon et al. |
| 2016/0309785 A1 | 10/2016 | Holtz |
| 2016/0309786 A1 | 10/2016 | Holtz et al. |
| 2016/0374397 A1 | 12/2016 | Jordan et al. |
| 2017/0045994 A1* | 2/2017 | Murison ............ H05B 47/105 |
| 2017/0258135 A1 | 9/2017 | Yerkic-Husejnovic et al. |
| 2017/0325502 A1 | 11/2017 | Nelson et al. |
| 2018/0280640 A1* | 10/2018 | Baker .................. A24F 47/008 |
| 2018/0338529 A1 | 11/2018 | Weigensberg et al. |

OTHER PUBLICATIONS

Faulwaser Michael et al., "10 Gbit/s Bidirectional Optical Wireless Communication Module for Docking Devices", 2014 IEEE Globecom Workshops (GC WKSHPS)—Optical Wireless Communications, pp. 512-517, Dec. 8, 2014.
Written Opinion of the International Preliminary Examining Authority dated Jan. 24, 2020 in International Application No. PCT/EP2019/055456.
International Preliminary Report on Patentability dated Apr. 8, 2020 in International Application No. PCT/EP2019/055456.

* cited by examiner

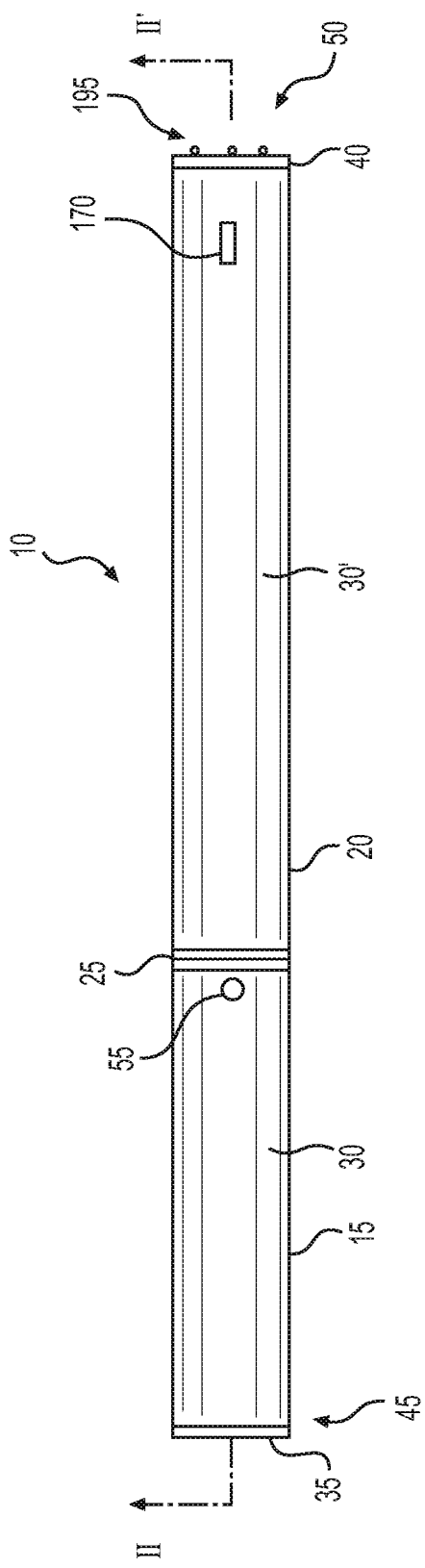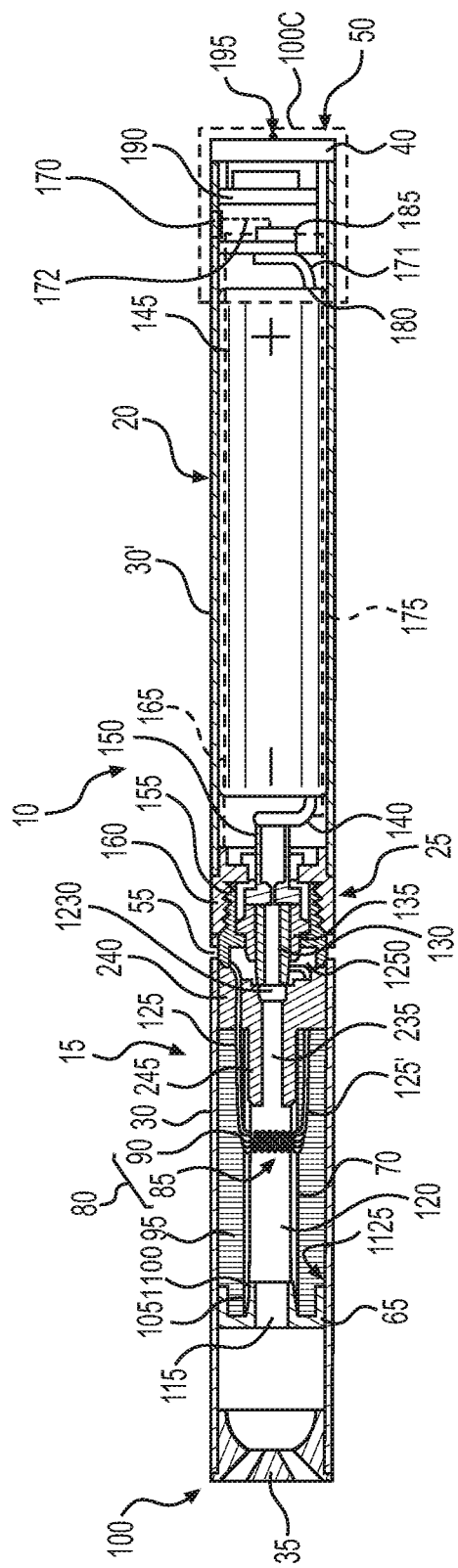

METHODS AND DEVICES FOR COMMUNICATION OF DATA BETWEEN ELECTRONIC VAPING DEVICE AND EXTERNAL DEVICE

BACKGROUND

Field

At least some example embodiments relate generally to electronic vaping (e-vaping) devices.

Related Art

An electronic vaping (e-vaping) device may include a cartridge portion and a power supply (or battery) portion. In this case, the cartridge portion attaches to the power supply portion to enable vaping by an adult vaper.

SUMMARY

At least one example embodiment provides an electronic vaping device comprising: a memory; a light emitting device configured to optically transmit information associated with the electronic vaping device to an external device; and processing circuitry coupled to the memory and the light emitting device. The processing circuitry is configured to: collect the information associated with the electronic vaping device; store the information in the memory; detect a triggering event; and initiate optical transmission of the information by the light emitting device in response to detecting the triggering event.

According to at least some example embodiments, the light emitting device may be a light emitting diode.

The processing circuitry may be further configured to encode the information as one or more light patterns, and the light emitting device may be configured to optically transmit the information by emitting the one or more light patterns.

The processing circuitry may be further configured to encode the information as the one or more light patterns by selecting at least one color of light from among a plurality of colors of light, and selecting at least one pattern of emission of the at least one color of light.

The processing circuitry may be further configured to encode the information by assigning one or more codes to the information, and the light emitting device may be configured to optically transmit the information by transmitting light signals representing the one or more codes.

The processing circuitry may be further configured to encode the information into a binary code, and the light emitting device may be configured to optically transmit the information by transmitting light signals representing the binary code.

The triggering event may be placement of the electronic vaping device into the external device, contacting the electronic vaping device with the external device, or establishing visual communication between the light emitting device and an optical sensor in the external device.

The electronic vaping device may further include an interface configured to generate a resistance when the interface contacts a corresponding interface of the external device, and to send the resistance to the processing circuitry as the triggering event.

The external device may be a personal charging case configured to charge the electronic vaping device.

The information may include at least one of: a number of applications of negative pressure to the electronic vaping device, a charge status of a battery of the electronic vaping device, an identification of the electronic vaping device, or a status of remaining pre-vapor formulation in a cartridge of the electronic vaping device.

The information may include vapor topography data.

The memory may store computer-readable instructions, and the processing circuitry may be a processor. The processor may be configured to execute the computer-readable instructions to: collect the information associated with the electronic vaping device, store the information in the memory, detect the triggering event, and initiate the optical transmission of the information by the light emitting device in response to detecting the triggering event.

The electronic vaping device may further include: a power supply configured to supply power to the electronic vaping device; a reservoir configured to hold a pre-vapor formulation; a heating element configured to heat pre-vapor formulation drawn from the reservoir; and a sensor coupled to the processing circuitry. The sensor may be configured to detect a pressure drop across the sensor, and to activate the electronic vaping device in response to the pressure drop.

At least one other example embodiment provides an apparatus comprising: a first slot configured to receive a first electronic vaping device; an optical sensor arranged in the first slot, the optical sensor configured to receive light signals from the first electronic vaping device, the light signals indicative of information associated with the first electronic vaping device; and processing circuitry. The processing circuitry is configured to: process the light signals to obtain the information associated with the first electronic vaping device, and generate an output based on the information associated with the first electronic vaping device.

The light signals may include a light pattern representing the information associated with the first electronic vaping device.

The apparatus may further include a memory storing a plurality of light patterns. The processing circuitry may be configured to decode the light pattern by comparing the light pattern to the plurality of light patterns stored in the memory.

Each of the plurality of light patterns may be a combination of one of a plurality of light colors emitted at one of a plurality of frequencies.

Each combination of one of the plurality of light colors and one of the plurality of frequencies may correspond to one type of information associated with the first electronic vaping device.

The light signals may represent a binary code; and the processing circuitry may be further configured to decode the binary code to obtain the information.

The processing circuitry may be further configured to decode the light signals to obtain the information associated with the first electronic vaping device.

The apparatus may further include a memory storing a codebook and coupled to the processing circuitry. The processing circuitry may be further configured to decode the light signals according to the codebook.

The output may indicate a status of the first electronic vaping device.

The apparatus may further include a memory coupled to the processing circuitry. The processing circuitry may be configured to store the information in the memory.

The processing circuitry may be further configured to initiate operation of the optical sensor in response to a triggering event.

The triggering event may be placement of the first electronic vaping device within the first slot.

The triggering event may be contacting the first electronic vaping device with the apparatus.

The triggering event may be expiration of a timer or establishing visual communication between the optical sensor and a light emitting device of the first electronic vaping device.

The information may include vapor topography data.

The information may include at least one of: a number of applications of negative pressure to the first electronic vaping device, a charge status of a battery of the first electronic vaping device, an identification of the first electronic vaping device, or a status of remaining pre-vapor formulation in a cartridge of the first electronic vaping device.

The apparatus may further include: a body including the first slot; and a cover element having at least one hollow section corresponding to at least the first slot, the at least one hollow section configured to receive a portion of the first electronic vaping device that extends out of the first slot when inserted therein, the cover element being configured to be opened and closed, the cover element covering the body when closed.

The apparatus may further include: a second slot configured to receive a second electronic vaping device; and a divider configured to separate the first slot from the second slot, the optical sensor and the processing circuitry positioned on the divider.

The apparatus may further include a display coupled to the processing circuitry, the processing circuitry further configured to drive the display to display the information.

The apparatus may further include an audio output coupled to the processing circuitry. The processing circuitry may be further configured to drive the audio output to output audio signals indicative of the information.

The apparatus may further include: a first battery; and a charger input to connect the apparatus to an external power source. The processing circuitry may be further configured to enable a charging of a battery of the first electronic vaping device via at least one of the first battery or the external power source.

BRIEF DESCRIPTION OF THE DRAWINGS

Example embodiments will become more apparent by describing the example embodiments in detail with reference to the attached drawings. The accompanying drawings are intended to depict example embodiments and should not be interpreted to limit the intended scope of the claims. The accompanying drawings are not to be considered as drawn to scale unless explicitly noted.

FIG. 1A is a side view of an electronic vaping (e-vaping) device according to an example embodiment;

FIG. 1B is a cross-sectional view along line II-II' of the e-vaping device shown in FIG. 1A according to an example embodiment;

DETAILED DESCRIPTION

Some detailed example embodiments are disclosed herein. However, specific structural and functional details disclosed herein are merely representative for purposes of describing example embodiments. Example embodiments may be embodied in many alternate forms and should not be construed as limited to only the embodiments set forth herein.

Figure 1C:
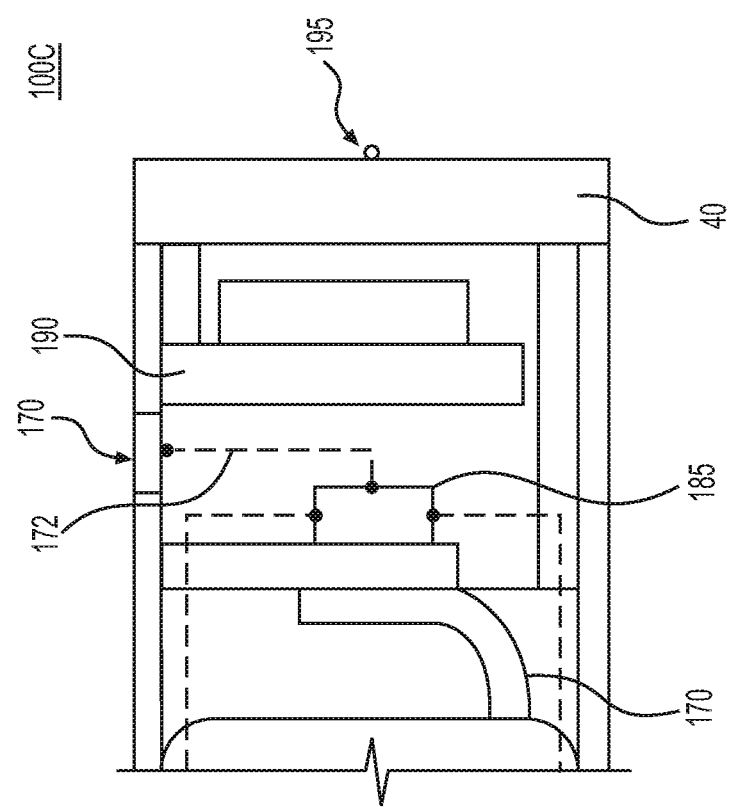
FIG. 1C is an enlarged view of a section of the e-vaping device shown in FIG. 1B according to an example embodiment.

FIG. 1A is a side view of an electronic vaping (e-vaping) device 10 according to an example embodiment. FIG. 1B is a cross-sectional view along line II-II' of the e-vaping device 10 of FIG. 1A according to an example embodiment. FIG. 1C is an enlarged view of section 100C of the e-vaping device 10 shown in FIG. 1B according to an example embodiment.

In addition to the features discussed herein, the e-vaping device 10 may include features set forth in U.S. Patent Application Publication No. 2013/0192623, filed Jan. 31, 2013 and/or features set forth in U.S. patent application Ser. No. 15/135,930, filed Apr. 22, 2016, the entire contents of each of which are incorporated herein by reference. According to one or more example embodiments, the e-vaping device 10 may also include features set forth in U.S. patent application Ser. No. 15/135,923 filed Apr. 22, 2016, and/or U.S. Pat. No. 9,289,014 issued Mar. 22, 2016, the entire contents of each of which are incorporated herein by reference. Although discussed herein with regard to e-vaping devices including a vaporizer assembly, example embodiments may also be applicable to other devices, such as, but without limitation, e-vaping devices including a dispersion generator configured to convert a pre-dispersion formulation into a dispersion, or other electronic devices.

Referring to FIG. 1A, the e-vaping device 10 may include a replaceable cartridge (or first section) 15 and a reusable power supply section (also referred to as a battery section or second section) 20, which may be removably coupled together at a threaded connector 25. Although example embodiments are shown and described with regard to a threaded connector, it should be appreciated that the connector 25 may be any type of connector, such as a snug-fit, detent, clamp, bayonet, and/or clasp. One or more air inlets 55 may extend through a portion of the connector 25 or through other locations in the first or second section.

In at least some example embodiments, the connector 25 may be a connector as described in U.S. application Ser. No. 15/154,439, filed May 13, 2016, the entire contents of which are incorporated herein by reference.

The first section 15 may include a first housing 30 and the second section 20 may include a second housing 30'. The e-vaping device 10 further include an outlet-end insert 35 at a first end 45 thereof. The first end 45 of the e-vaping device 10 may be referred to herein as an "outlet end" of the e-vaping device 10.

In the example embodiments shown in FIGS. 1A-1C, the first housing 30 and the second housing 30' may have a generally cylindrical cross-section. However, one or more of the first housing 30 and the second housing 30' may alternatively have a generally triangular cross-section or other shapes. Furthermore, the first housing 30 and the second housing 30' may have the same or different cross-section shape, or the same or different size. As discussed herein, the first housing 30 and the second housing 30' may also be referred to as outer or main housings.

As described further below with regard to FIG. 1B, each of the first housing 30 and the second housing 30' defines an interior ("interior space") of at least a portion of the e-vaping device 10 and in which one or more elements of the e-vaping device 10 are included.

The e-vaping device 10 further include an end cap 40 at a second end 50 of the e-vaping device 10. The second end 50 may be referred to herein as a "tip end" of the e-vaping device 10. Although not shown, the e-vaping device 10 may include a light at the second end 50 of the e-vaping device 10.

The e-vaping device 10 may further include a light emitting diode (LED) 170 and an interface 195 at the second end 50 of the e-vaping device 10. In this example, the LED 170 is arranged at or on the outer shell of the second housing 30', such that the LED 170 is configured to emit light signals external to the e-vaping device 10. The interface 195 may include electrical contact pins exposed and/or extending through the end cap 40. In at least one other example embodiment, the interface 195 may include inductive charging circuitry, in addition, or as an alternative to, the electrical contact pins. The LED 170 and the interface 195 will be discussed in more detail later.

As shown in FIG. 1B, the first section 15 includes a reservoir 95 configured to store a pre-vapor formulation and a vaporizer 80 (also referred to herein as a "vaporizer assembly") to vaporize the pre-vapor formulation to form a generated vapor. Forming a generated vapor may be referred to herein as "generating a vapor," "vapor generation," or the like. Vaporizing the pre-vapor formulation may include heating the pre-vapor formulation to cause the pre-vapor formulation to vaporize.

The vaporizer 80 includes a heating element 85 and a wick 90 to draw the pre-vapor formulation from the reservoir 95. The heating element 85 may be referred to interchangeably herein as a "heater."

According to one or more example embodiments, the pre-vapor formulation is a material or combination of materials that may be transformed into a vapor ("generated vapor"). For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol.

Still referring to FIG. 1B, the first housing 30 extends in a longitudinal direction, and an inner tube (or chimney) 70 is coaxially positioned within the first housing 30.

The e-vaping device 10 further includes a first connector piece 155. In at least this example embodiment, the first connector piece 155 includes a male threaded section for connecting the first section 15 and the second section 20. However, example embodiments should not be limited to this example.

At an upstream end portion of the inner tube 70, a nose portion 245 of a gasket (or seal) 240 is fitted into the inner tube 70, and an outer perimeter of the gasket 240 provides a seal with an interior surface of the first housing 30. The gasket 240 has a central, longitudinal air passage 235 in fluid communication with the inner tube 70 to define an inner passage (also referred to as a central channel or central inner passage) 120. A transverse channel 1230 at a backside portion of the gasket 240 intersects and communicates with the air passage 235 of the gasket 240. This transverse channel 1230 ensures communication between the air passage 235 and a space 1250 defined between the gasket 240 and the first connector piece 155.

The one or more air inlets 55 are arranged on the first housing 30 in relatively close proximity to the connector 25 (e.g., adjacent the connector 25). In another example, the air inlets 55 may be provided on the connector 25 instead of the first housing 30. The air inlets 55 may be sized and configured such that the e-vaping device 10 has a resistance-to-draw (RTD) in the range of from about 60 mm $H_2O$ to about 150 mm $H_2O$.

A nose portion 1100 of a gasket 65 is fitted into a first end portion 105 of the inner tube 70. An outer perimeter of the gasket 65 provides a substantially tight seal with an interior surface 1125 of the first housing 30. The gasket 65 includes a central channel 115 disposed between the inner passage 120 of the inner tube 70 and the interior of the outlet-end insert 35, to transport the vapor from the inner passage 120 to the outlet-end insert 35.

According to at least some example embodiments, the outlet-end insert 35 may include one outlet 100 that may coincide with the longitudinal axis of the e-vaping device 10 and/or one, two, or more outlets 100 located off-axis from the longitudinal axis of the e-vaping device 10. One or more outlets 100 may be angled outwardly in relation to the longitudinal axis of the e-vaping device 10. One or more outlets 100 may be substantially uniformly (e.g., uniformly within manufacturing tolerances and/or material tolerances) distributed about the perimeter of the outlet-end insert 35 so as to substantially uniformly distribute vapor.

The space defined between the gasket 65, the gasket 240, the first housing 30 and the inner tube 70 establishes the confines of the reservoir 95. The reservoir 95 may contain a pre-vapor formulation, and optionally a storage medium (not shown) configured to store the pre-vapor formulation therein. The storage medium may include a winding of cotton gauze or other fibrous material about the inner tube 70.

The reservoir 95 at least partially surrounds the inner passage 120. The reservoir 95 may be sized and configured to hold enough pre-vapor formulation such that the e-vaping device 10 may be configured for vaping for a threshold (e.g., certain or desired) amount of time, such as, for example, at least about 200 seconds. Moreover, the e-vaping device 10 may be configured to allow each application of negative pressure (or draw of vapor through an outlet) to last a certain maximum of time, such as for example, about 5 seconds.

In at least some example embodiments, the storage medium may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns), but other sizes may be used. In at least some example embodiments, the storage medium may be a sintered, porous or foamed material, or combinations thereof. Also, the fibers may be sized to be irrespirable and may have a cross-section that has a Y-shape, cross shape, clover shape or any other suitable shape. In at least some example embodiments, the reservoir 95 may include a filled tank lacking any storage medium and containing only pre-vapor formulation.

The heating element 85 extends transversely across the inner passage 120 between opposing portions of the reservoir 95. In at least some other example embodiments, however, the heating element 85 may extend parallel to a longitudinal axis of the inner passage 120.

During generation of vapor ("an instance of vapor generation"), pre-vapor formulation is transferred from the reservoir 95 and/or storage medium to proximity of the heating element 85 via capillary action of the wick 90. The wick 90 includes at least a first end portion and a second end portion, which extend into opposite sides of the reservoir 95. The heating element 85 at least partially surrounds a central portion of the wick 90 such that when the heating element 85 is activated, the pre-vapor formulation in the central portion of the wick 90 is vaporized by the heating element 85 to form a vapor.

According to at least some example embodiments, the wick 90 may include filaments (or threads) having a capacity to draw the pre-vapor formulation. For example, the wick 90 may be a bundle of glass (or ceramic) filaments, a bundle including a group of windings of glass filaments, or the like, all of which arrangements may be capable of drawing pre-vapor formulation via capillary action by interstitial spacings between the filaments. The filaments may be generally aligned in a direction perpendicular (transverse) to the longitudinal direction of the e-vaping device 10. In at least some example embodiments, the wick 90 may include one to eight (or more) filament strands, each strand comprising a plurality of glass filaments twisted together. The end portions of the wick 90 may be flexible and foldable into the confines of the reservoir 95. The filaments may have a cross-section that is generally cross-shaped, clover-shaped, Y-shaped, or in any other suitable shape.

According to at least some example embodiments, the wick 90 may include any suitable material or combination of materials. Examples of suitable materials may be, but not limited to, glass, ceramic- or graphite-based materials. The wick 90 may have any suitable capillary drawing action to accommodate pre-vapor formulations having different physical properties such as density, viscosity, surface tension and vapor pressure. The wick 90 may be non-conductive.

According to at least some example embodiments, the heating element 85 may include a wire coil ("heater coil"), which at least partially surrounds the wick 90. The wire may be a metal wire and/or the heater coil may extend fully or partially along the length of the wick 90. The heater coil may further extend fully or partially around the circumference of the wick 90. In at least some example embodiments, the heating element 85 may or may not be in contact with the wick 90.

The heating element 85 may heat pre-vapor formulation in the wick 90 by thermal conduction. In at least some example embodiments, heat from the heating element 85 may be conducted to the pre-vapor formulation by a heat conductive element or the heating element 85 may transfer heat to the incoming ambient air that is drawn through the e-vaping device 10 during vaping, which in turn heats the pre-vapor formulation by convection.

It should be appreciated that, instead of using a wick 90, the heating element 85 may include a porous material that incorporates a resistance heater formed of a material having a relatively high electrical resistance capable of generating heat relatively quickly.

Although discussed with regard to the heating element 85 being in the form of a wire coil, the heating element 85 may alternatively be in the form of a planar body, a ceramic body, a single wire, a cage of resistive wire or any other suitable form. In this regard, the heating element 85 may be any heater that is configured to vaporize a pre-vapor formulation.

Although discussed herein with regard to a wick and a heater, example embodiments should not be limited to this example. Rather, example embodiments may include a capillary tube or passage through which the pre-vapor formulation is transferred from the reservoir 95 and/or storage medium, and heated. In at least this example embodiment, at least a portion of the capillary tube or passage may heat the pre-vapor formulation to generate a vapor, and output the generated vapor.

The heater and/or heater coil may be formed of and/or may at least partially comprise any suitable electrically resistive materials. Examples of suitable electrically resistive materials may include, but are not limited to, copper, titanium, zirconium, tantalum and metals from the platinum group. Examples of suitable metal alloys include, but are not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 85 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 85 may include at least one material selected from the group consisting of or including stainless steel, copper, copper alloys, nickel-chromium alloys, super alloys and combinations thereof. In at least some example embodiments, the heating element 85 may be formed of nickel-chromium alloys or iron-chromium alloys. In at least some example embodiments, the heating element 85 may be a ceramic heater having an electrically resistive layer on an outside surface thereof.

Still referring to FIGS. 1A and 1B, the inner tube 70 includes a pair of opposing slots, such that the wick 90 and a first electrical lead 125 and a second electrical lead 125' (or alternatively ends of the heating element 85 itself) may extend out from the respective opposing slots. The provision of the opposing slots in the inner tube 70 may facilitate placement of the heating element 85 and wick 90 into position within the inner tube 70 without impacting edges of the slots and the coiled section of the heating element 85. In at least some example embodiments, edges of the slots may not be allowed to impact and alter the coil spacing of the heating element 85, which would otherwise create potential sources of hotspots. In at least some example embodiments, the inner tube 70 may have a diameter of about 4 mm and each of the opposing slots may have major and minor dimensions of about 2 mm by about 4 mm.

The first electrical lead 125 is physically and electrically connected to the male threaded connector piece 155. As shown, the male threaded first connector piece 155 is a hollow cylinder with male threads on a portion of the outer lateral surface. The first connector piece 155 is conductive, and may be formed of or coated with a conductive material.

The second electrical lead 125' is physically and electrically connected to a first conductive post 130. The first conductive post 130 may be formed of a conductive material (e.g., stainless steel, copper, or the like), and may have a T-shaped cross-section. The first conductive post 130 nests within the hollow portion of the first connector piece 155, and may be electrically insulated from the first connector piece 155 by an insulating shell 135. In the example embodiment shown in FIG. 1B, the first conductive post 130 may be hollow, and the hollow portion may be in fluid communication with the inner passage 120. Accordingly, the first connector piece 155 and the first conductive post 130 form respective external electrical connection to the heating element 85.

The second section 20 includes a female threaded second connector piece 160 at an end opposite to the second (or tip) end 50 of the e-vaping device 10 (sometimes referred to herein as a connector end of the second section 20). The second connector piece 160 has a hollow cylinder shape with threading on an inner lateral surface. The inner diameter of the second connector piece 160 matches that of the outer diameter of the first connector piece 155 such that the two connector pieces 155, 160 may be threaded together to connect the first section 15 with the second section 20. Furthermore, the second connector piece 160, or at least the lateral surface may be conductive, for example, formed of or including a conductive material. As such, an electrical and physical connection may occur between the first and second connector pieces 155, 160 when connected.

While example embodiments are discussed herein with regard to male threaded connector piece 155 and female threaded connector piece 160, example embodiments are not limited thereto. For example, the male threaded connector piece 155 may be associated with the second section 20 and the female threaded connector piece 160 may be associated with the first section 15.

As shown in FIGS. 1B and 1C, the second section 20 further includes a power supply 145, a controller 185 (also referred to as "control circuitry") and a sensor 190. As mentioned above, the LED 170 and the interface 195 are also included in the second section 20. As shown, the power supply 145, the controller 185 and the sensor 190 are disposed in the second housing 30'. Further, as mentioned above with regard to FIG. 1A, the LED 170 is arranged at the outer portion of the second housing 30', such that light from the LED 170 is emitted externally from the e-vaping device 10. The interface 195 is at (and may be exposed through) the second (or tip) end 50.

A first lead 165 electrically connects the second connector piece 160 to the controller 185. A second lead 171 electrically connects the controller 185 to a first terminal 180 of the power supply 145. A third lead 175 electrically connects a second terminal 140 of the power supply 145 to the power terminal of the controller 185 to provide power to the controller 185. A fourth lead 172 electrically connects the controller 185 to the LED 170, and a fifth lead (173 in FIG. 4) electrically connects the controller 185 to the interface 195.

The second terminal 140 of the power supply 145 is also physically and electrically connected to a second conductive post 150. The second conductive post 150 may be formed of a conductive material (e.g., stainless steel, copper, or the like). In the example embodiment shown in FIG. 1B, the second conductive post 150 may have a T-shaped cross-section and is hollow. The second conductive post 150 nests within the hollow portion of the second connector piece 160, and is electrically insulated from the second connector piece 160 by an insulating shell. When the first and second connector pieces 155, 160 are coupled to one another, the second conductive post 150 physically and electrically connects to the first conductive post 130. Also, the hollow portion of the second conductive post 150 is in fluid communication with the hollow portion of the first conductive post 130.

According to at least some example embodiments, the power supply 145 may be, or include, a battery. The battery may be a Lithium-ion battery or variant thereof, for example a Lithium-ion polymer battery. In at least some other example embodiments, the power supply 145 may be a nickel-metal hydride battery, a nickel cadmium battery, a lithium-manganese battery, a lithium-cobalt battery or a fuel cell. The e-vaping device 10 may be controlled to generate vapor, based on adult vaper interaction with the e-vaping device 10, until the energy in the power supply 145 is depleted or a minimum voltage cut-off level is achieved. The power supply 145 may be rechargeable. For example purposes, the power supply 145 will be discussed as a rechargeable battery.

Still referring to FIGS. 1B and 1C, the second section 20 may include circuitry configured to allow the battery to be charged by an external charging device, such as a PCC as described in more detail later with regard to FIGS. 2A-2C, via the interface 195, for example.

The sensor 190 is configured to generate an output indicative of a magnitude and/or direction of airflow through the e-vaping device 10. For example, and without limitation, the controller 185 may receive an output of the sensor 190, and determines if (1) the direction of the airflow indicates application of negative pressure on the outlet-end insert 35 and (2) the magnitude of the application of negative pressure (e.g., a magnitude of the flow rate of the airflow) exceeds a threshold level. When these or other vaping conditions are met, then the controller 185 may be understood to have received, from the sensor 190, sensor data that amounts to a vapor generation command. The sensor 190 may be a sensor as disclosed in U.S. application Ser. No. 14/793,453, filed on Jul. 7, 2015, or a sensor as disclosed in U.S. Pat. No. 9,072,321, issued on Jul. 7, 2015, the entire contents of each of which is incorporated herein by reference.

The e-vaping device 10 may include an interface with which an adult vaper may interact to cause a vapor generation command to be transmitted to the controller 185. Based on a determination that a vapor generation command is received at the controller 185, the controller 185 may electrically connect the power supply 145 to the heating element 85, thereby supplying power to, and activating, the heating element 85. In more detail, for example, the controller 185 may electrically connect the first and second leads 165, 171 (e.g., by activating a heater power control transistor forming part of the controller 185) such that the heating element 85 electrically connects to the power supply 145. In at least some example embodiments, the sensor 190 may indicate a pressure drop, and the controller 185 may activate the heating element 85 in response the indicated pressure drop.

Example operation of an example e-vaping device to create a vapor ("vapor generation") will now be described. According to at least one example embodiment, air is drawn primarily into the first section 15 through the at least one air inlet 55 in response, for example, to application of negative pressure to the outlet-end insert 35 by an adult vaper. Air passes through the air inlet 55, into the space 1250, through the transverse channel 1230 into the air passage 235, into the inner passage 120, and through the outlet(s) 100 of the outlet-end insert 35. If the controller 185 detects the vaping conditions discussed above (e.g., based on determining that a magnitude of airflow, as indicated by signals ("sensor data") generated by sensor 190, at least meets a threshold level), then the controller 185 initiates power supply to the heating element 85, such that the heating element 85 heats pre-vapor formulation in the wick 90. The vapor and air flowing through the inner passage 120 combine and exit the e-vaping device 10 via the outlet(s) 100 of the outlet-end insert 35.

In at least some example embodiments, when activated, the heating element 85 may heat a portion of the wick 90 for less than a threshold or certain amount of time, for example, for less than about 10 seconds.

In at least some example embodiments, the first section 15 may be a replaceable cartridge. Once the pre-vapor formulation in the reservoir 95 is depleted, the first section 15 may be replaced and the replacement may be used with the second section 20, which may be reusable. In at least some other example embodiments, the entire e-vaping device 10 may be disposed once the reservoir 95 is depleted. In this case, the e-vaping device 10 may be a one-piece e-vaping device.

In at least some example embodiments, the e-vaping device 10 may be about 80 mm to about 110 mm long and about 7 mm to about 8 mm in diameter. For example, in at least some example embodiments, the e-vaping device 10 may be about 84 mm long and may have a diameter of about 7.8 mm. Other dimensions may also be used.

Still referring to FIGS. 1B and 1C, as mentioned above, the LED 170 is located proximal to the second end 50 of the e-vaping device 10. In at least one example embodiment, the LED 170 is positioned to align with an optical sensor (also referred to as a light sensor) in a slot of a personal charging case (PCC) as will be discussed in more detail later. Although example embodiments will be discussed herein with regard to the LED 170 positioned proximal to the second end 50, example embodiments should not be limited to this example. Rather, the LED 170 may be located proximal to the connector 25 of the second section 20, on the first section 15, or at any other location of the e-vaping device 10 to be aligned with an optical sensor when inserted into a slot of a PCC. Additionally, although discussed herein with regard to a LED 170, any other suitable light emitting device may be used.

According to one or more example embodiments, the controller 185 may control various functions of the e-vaping device 10. Additionally, the controller 185 may be configured to monitor, collect and/or store various information associated with the e-vaping device 10, encode the stored information, and/or control the LED 170 to optically transmit light signals representing the monitored, collected and stored information to, for example, a PCC, which will be further described below.

In one example, the monitored, collected and/or stored information may include vapor topography data generated by a topography apparatus as described in, for example, U.S. application Ser. No. 15/604,500, filed May 24, 2017, the entire contents of which are incorporated herein by reference.

As described herein, vapor topography data (also referred to as topography data) may include information indicating a physical characteristic of a pattern of vapor generation by the e-vaping device 10. Such a pattern may be associated with a particular adult vaper that may interact with the e-vaping device 10 to cause the e-vaping device 10 to generate vapor according to a particular pattern of vapor generation. For example, vapor topography data may include information indicating a physical characteristic of a pattern of vapor generation by the e-vaping device 10, where such a physical characteristic may include time stamps at which discrete instances of vapor generation by the e-vaping device 10 occur, a frequency at which discrete generations of vapor by the e-vaping device 10 occur over a particular time period, a determined magnitude of vapor generated by the e-vaping device 10 (e.g., for each discrete instance of vapor generation and/or an average for a particular quantity of vapor generations over a particular period of time), a determined magnitude of a flow rate of air and/or vapor through one or more portions of the e-vaping device 10 concurrently with one or more discrete generations of vapor by the e-vaping device 10, a voltage output of a power supply of the e-vaping device 10 in association with generation of vapor by the e-vaping device 10, a presence and/or amount and/or density of one or more particular volatile organic compounds (VOCs) in a vapor generated by the e-vaping device 10, etc., some combination thereof, or the like.

Vapor topography data may also include statistical information generated based on processing one or more various signals, received from one or more elements within the interior of the e-vaping device 10, over a period of time. For example, vapor topography data may indicate a statistical distribution (e.g., a normal distribution) of vapor generation durations for a given period of time (e.g., a 24-hour period, a week, a month, or other time period).

In at least some example embodiments, the information may also, or alternatively, include at least one of a number of applications of negative pressure (puff events), a charge status of a battery of the e-vaping device 10, an identification of the e-vaping device 10, a status of a remaining pre-vapor formulation in the first section 15 of the e-vaping device 10, or the like.

Still referring to FIGS. 1B and 1C, as mentioned above, the interface 195 may be arranged at the second end 50 of the e-vaping device 10. In some example embodiments, the electrical pins of the interface 195 may be exposed at the tip end 50 of the e-vaping device 10, and may be complementary to an electrical interface (e.g., electrical pins) of the PCC. As mentioned above, as an alternative, the interface 195 may include inductive or wireless charging circuitry. In at least this example, the electrical pins and the complementary electrical pins of the PCC may be omitted.

The interface 195 may facilitate transfer of power from a power source (e.g., a PCC battery and/or an external power source connected to the PCC) to the power supply 145 of the e-vaping device 10.

According to at least one example embodiment, the interface 195 may include processing circuitry and at least one resistive element (collectively referred to as circuitry). In one example, the circuitry may be utilized to generate a resistance when the e-vaping device 10 is inserted in, and a physical connection is established with, a corresponding interface of the PCC. In at least one example embodiment, the circuitry may be further configured to send the generated resistance to the controller 185 to indicate the established connection, and the controller 185 may detect the established physical connection between the e-vaping device 10 and the PCC based on the generated resistance. As discussed in more detail later, this may constitute a triggering event.

According to at least one example embodiment, and for purposes of detecting the above-described physical connection(s) and/or generating the above-described resistance, the interface 195 may operate as set forth in U.S. patent application Ser. No. 15/067,323, filed Mar. 11, 2016, the entire contents of which are incorporated herein by reference.

Figure 4:
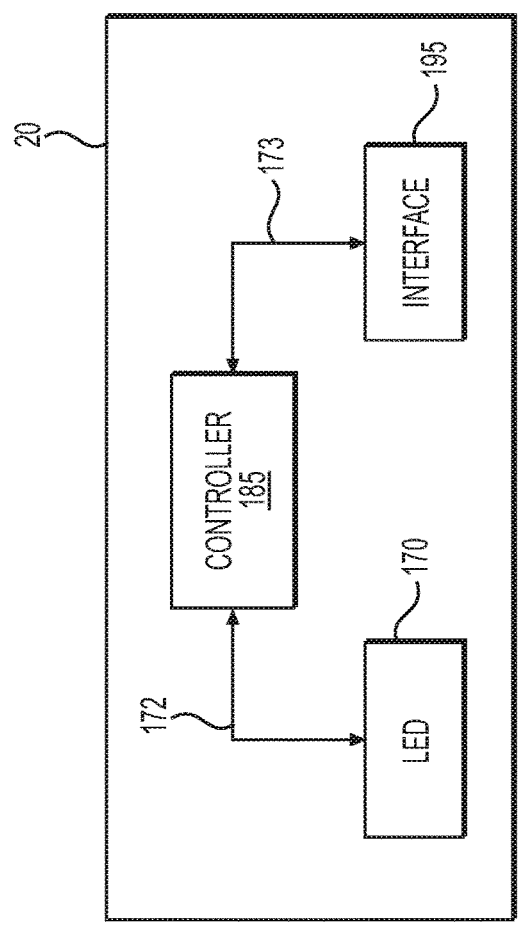
FIG. 4 is a block diagram illustrating example electrical connections between various components of the second section of the e-vaping device shown in FIGS. 1A-1C.

FIG. 4 is a diagram of electrical connections among various components of the second section 20 of the e-vaping device 10 shown in FIGS. 1A-1C, according to an example embodiment. As shown in FIG. 4, the controller 185 is connected to, among other things, the LED 170 via fourth lead 172 and the interface 195 via fifth lead 173. Although not shown, the controller 185, the LED 170 and the interface 195 may also be connected to the power supply 145, as well as components of the first section 15 (e.g., the heater) when the second section 20 is connected to the first section 15.

In one example, in response to detecting a trigger event, the controller 185 may encode stored information associated with the e-vaping device 10, and operate the LED 170 to optically transmit the encoded information to a PCC (or other external device). Example operation of an example controller 185 and an example LED 170 will be discussed in more detail later with regard to FIG. 6.

Figure 5:
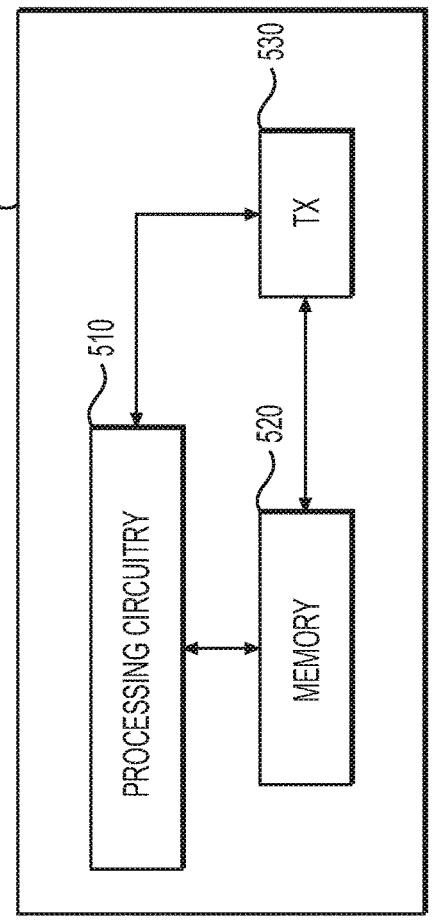
FIG. 5 illustrates an example embodiment of a controller of the e-vaping device embodiments shown in FIGS. 1A-1C.

FIG. 5 illustrates an example embodiment of the controller 185 shown in FIGS. 1B, 1C and 4.

As shown in FIG. 5, the controller 185 includes a processor 510, a memory 520 and a transceiver 530. The processor 510, the memory 520 and the transceiver 530 may be communicatively coupled to one another.

In at least one example embodiment, the processor 510 may monitor various types of information regarding the e-vaping device 10. The processor 510 may store the monitored information in the memory 520. In at least one example embodiment, the processor 510 may retrieve the stored information from the memory 520, encode the retrieved information, and transfer the encoded information to an external device (e.g., a PCC) via the LED 170, for example, in response to detecting a triggering event, as will be described in more detail below.

In at least one example embodiment, the processing circuitry 510 may include at least one processor. In this example, the processor may be any known, or to be developed, processor configured to execute computer-readable instructions stored on the memory 520. Execution of the computer-readable instructions stored on the memory 520 transforms the at least one processor into a special purpose processor for carrying out the functionality described herein. The memory 520 may be further configured to store various types of information regarding the e-vaping device 10, such as that described above. As will be described below, such stored data may be encoded and transmitted to an optical sensor (e.g., at a PCC or other external device) via the LED 170.

Although discussed in some cases with regard to a processor and a memory, according to at least some example embodiments, the controller 185 (or control circuitry or processing circuitry) may be (or include) hardware, firmware, hardware executing software, or any combination thereof. For example, the controller 185 may include one or more Central Processing Units (CPUs), digital signal processors (DSPs), application-specific-integrated-circuits (ASICs), field programmable gate arrays (FPGAs), or other circuitry configured as special purpose machines to perform the functions of the controller 185. As mentioned above, example functionality of the controller 185 will be described in more detail below with regard to FIG. 6.

An example embodiment of a PCC as well as example interaction between a PCC and the e-vaping device 10 will be discussed in more detail with regard to FIGS. 2A-2C.

Figure 2A:
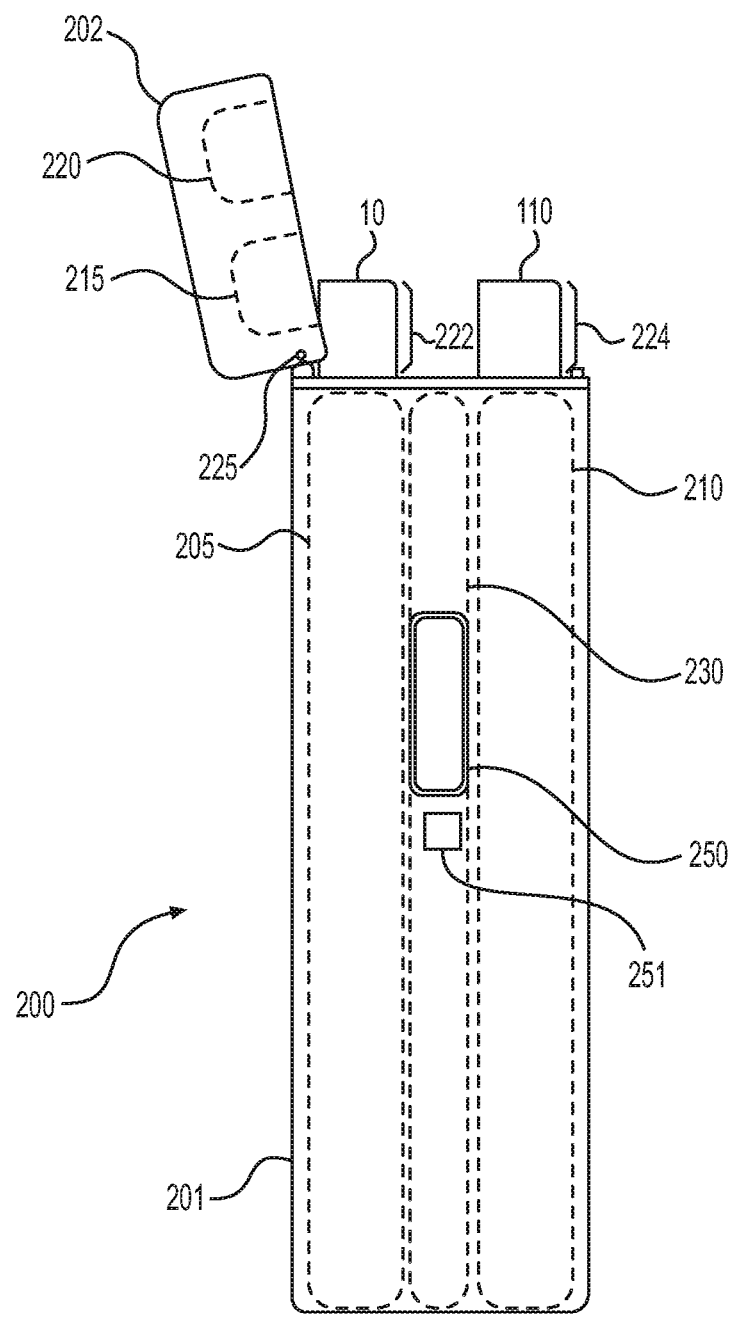
FIG. 2A illustrates an example embodiment of a personal charging case (PCC) for an electronic vaping device.

FIG. 2A illustrates an example embodiment of a PCC for an e-vaping device, such as the embodiments shown in FIGS. 1A-1C.

Referring to FIG. 2A, a PCC 200 includes a body element 201 (which may hereinafter be referred to as a PCC "body"). The body 201 include slots 205 and 210. Each of the slots 205 and 210 may be configured to receive one e-vaping device, such as the embodiments shown in FIGS. 1A-1C. While FIG. 2A illustrates the body 201 as having two slots to receive two e-vaping devices (e.g., an e-vaping device 10 in the slot 205 and a same or similar e-vaping device 110 in the slot 210), example embodiments are not limited to this example. Rather, the body 201 may include any number of slots (e.g., 1 slot, 3 slots, 4 slots, or the like).

The PCC 200 includes a cover element 202, which is also referred to herein as a PCC "cover". The cover 202 includes slots 215 and 220. Each of the slots 215 and 220 corresponds to one of the slots 205 and 210 in the body 201. Each of the slots 215 and 220 may be configured to receive a portion of an e-vaping device that extends outside of a corresponding one of the slots 205 and 210. The portion of an e-vaping device 10 extending outside of the slot 205 is indicated by the reference numeral 222 (hereinafter the extended portion 222) and the portion of e-vaping device 110 extending outside of the slot 210 is indicated by the reference numeral 224 (hereinafter the extended portion 224). Accordingly, each of the slots 205 and 210 in the body 201 together with a corresponding one of the slots 215 and 220 in the cover 202 collectively establish an enclosure in which the e-vaping device 10 or the e-vaping device 110 may be accommodated.

In at least one alternative example embodiment, instead of having slots 215 and 220, the cover 202 may have an empty/hollow section inside for covering the extended portions 222 and 224 of the e-vaping devices 100 and 110.

In the example embodiment shown in FIG. 2A, the cover 202 is attached to the body 201 via a hinge 225. In this example, the cover 202 rotates/pivots about the hinge 225 to allow the cover 202 to be opened and closed while remaining attached to the body 201. As an alternative, the cover 202 may be a removable cap, without a hinge, or any other suitable cover. The cover 202 completely covers an upper portion of the body 201 when the cover 202 is closed.

According to at least one example embodiment, the body 201 and the cover 202 of the PCC 200 may be made of metallic, plastic or any combination of suitable material or materials.

Still referring to FIG. 2A, the PCC 200 further includes a divider 230 that may separate the slots 205 and 210.

The body 201 of some example embodiments of PCC 200 may include a display 250 (e.g., on the exterior thereof). The display 250 may be any type of known, or to be developed, digital display. For example, the display 250 may be a liquid crystal display (LCD) display, a light emitting diode (LED) display, an organic LED (OLED) display, an electrophoretic (electronic paper (e-paper)) display, or the like. As will be described below, the display 250 may display information (provide a visual output or a visual indication) regarding PCC 200, e-vaping device 10 and/or e-vaping device 110, including, but not limited to, a status of the first section 15 of the e-vaping device 10 (or that of the e-vaping device 110), a status of the power supply 145 of the e-vaping device 10 (or that of the e-vaping device 110), a status of a battery of the PCC 200 and/or vapor topography data, etc. The status of the first section 15 may correspond to, for example and without limitation, the amount of pre-vapor formulation remaining inside the first section 15. The status of the power supply 145 may correspond to, for example and without limitation, the amount of charge remaining inside the battery of the power supply 145. The status of the battery of the PCC 200 may correspond to, for example and without limitation, the amount of charge remaining inside the battery of the PCC 200.

Some example embodiments of PCC 200 may include a speaker (audio output provider) 251. The speaker 251 may be any known, or to be developed, speaker capable of outputting audio signals (or audio indications). According to at least some example embodiments, various types of information regarding the PCC 200, the e-vaping device 10 and/or the e-vaping device 110 may be communicated by outputting audio signals through the speaker 251. In at least one example embodiment, the information conveyed via the display 250 may also (or alternatively) be conveyed in the form of audio signals or audio indications via the speaker 251.

Figure 2B:
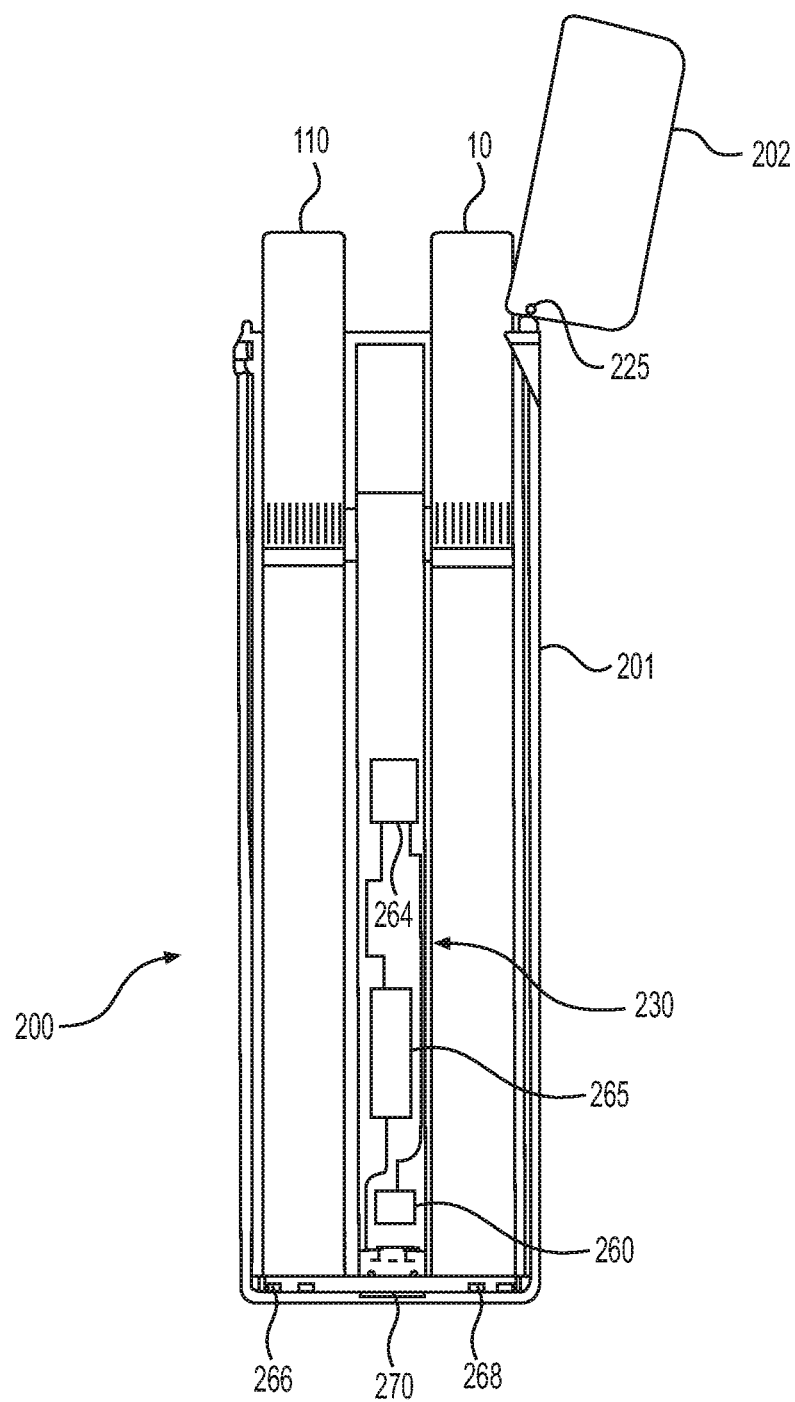
FIG. 2B illustrates an internal or cut-away view of the PCC shown in FIG. 2A according to an example embodiment.

FIG. 2B illustrates an example embodiment of an internal or cut-away view of PCC 200 shown in FIG. 2A. In the example embodiment shown in FIG. 2B, the two e-vaping devices 10 and 110 are inserted into the slots 205 and 210, respectively.

Referring to FIG. 2B, example embodiments of the PCC 200 further includes an optical sensor 260, a controller 264, a battery 265 (which may also be referred to as the PCC battery 265), interfaces 266 and 268 and a charger input 270. Connections between these, as well as other, components of the PCC 200 will be discussed in more detail later with regard to FIG. 2C.

While only one optical sensor 260 is shown in FIG. 2B, example embodiments are not limited thereto. In one example embodiment, the PCC 200 may have a separate optical sensor associated with each of the slots 205 and 210. In the example embodiment shown in FIG. 2B, the optical sensor 260, the controller 264 and the charger input 270 are located along the divider 230 within the body 201 of the PCC 200. The PCC battery 265 may also located along the divider 230 and in relatively close proximity to the controller 264. However, the exact positioning of the optical sensor 260, the controller 264, the PCC battery 265 and the charger input 270 is not limited to the example shown in FIG. 2B.

The optical sensor 260 is positioned to align with the position of the LED 170 of the e-vaping devices 10 and/or 110 when the e-vaping devices are inserted into respective slots 205 and 210. According to at least one example embodiment, the optical sensor 260 may be an electro-optical sensor, such as, a photoconductive device configured to convert a change of incident light into a change in resistance, a photodiode configured to convert incident light into an output current, or any other known, or to be developed, optical sensor capable of converting incident light into an electrical signal.

The controller 264, which will be further described below with reference to FIG. 3, may include a memory, processing circuitry (e.g., a processor or other integrated circuitry) and a transceiver. According to at least one example embodiment, the controller 264 may activate the optical sensor 260 in response to detecting that an e-vaping device 10 has been inserted into PCC 200, receive encoded information from e-vaping device 10 via the optical sensor 260, decode the received information, and then output or convey the decoded information to an external device (e.g., via a wired or wireless connection) or adult vaper via, for example, the display 250 and/or speaker 251. Example functionality of the controller 264 will be described in more detail below with reference to FIG. 7.

Returning to FIG. 2B, the PCC battery 265 may be any known, or to be developed, battery capable of powering a PCC 200, charging an e-vaping device inserted into the PCC 200 and/or being charged when the PCC 200 is connected to an external power source via the charger input 270. In at least one example embodiment, when an e-vaping device (e.g., e-vaping device 10) is inserted into the slot 205 or 210, the PCC battery 265 of the PCC 200 may charge the power supply 145 of the e-vaping device 10 via the corresponding one of the interfaces 266 and 268 (e.g., via electrical pins of the interface 266 or 268 configured to establish an electrical connection between the inserted e-vaping device 10 and the PCC 200). The pins of the interfaces 266 and 268 may be complementary to the pins of the interface 195.

The charger input 270 may be positioned at the bottom of the body 201 of the PCC 200. However, example embodiments are not limited thereto. The charger input 270 may be used for connecting the PCC 200 to an external power source for charging the PCC battery 265 and/or charging the power supply 145 in the e-vaping devices 10 and 110 once inserted into the PCC 200. According to at least one example embodiment, it may be possible to charge the power supply 145 either via the PCC battery 265 or via the external power source. According to at least some example embodiments, the charger input 270 may be a universal serial bus (USB) connection, such as a micro USB connection, USB-C connection, or the like, or any other type of suitable connection.

As shown in FIG. 2B, each of the interfaces 266 and 268 may be positioned at the bottom of the corresponding one of the slots 205 and 210. Upon placement of the e-vaping devices 10 and 110 into the slots 205 and 210, respectively, a physical (e.g., an electrical and/or mechanical) connection may be established between the inserted e-vaping device (or, more specifically, between the battery section of the inserted e-vaping device) and the corresponding interface via the corresponding pins, as described above.

Each of the interfaces 266 and 268 may have one or more pins through which an inserted e-vaping device such as the e-vaping device 10 may establish a connection (an electrical connection) to the PCC 200. The interfaces 266 and 268 (and pins thereof) may facilitate transfer of power from a power source (e.g., the PCC battery 265 of the PCC 200 and/or the external power source connected to the charger input 270) to a battery section (e.g., the power supply 145) of the respective e-vaping device 10 or 110.

In at least one example embodiment, each of the interfaces 266 and 268 may include processing circuitry and at least one resistive element (collectively referred to as circuitry). The circuitry may be utilized to generate a resistance when the e-vaping devices 10 and/or 110 is/are inserted in, and a physical connection is established with, the corresponding slots 205 and/or 210. The circuitry may be further configured to send the generated resistance to the controller 264 to indicate the established connection, and the controller 264 may detect the established physical connection between the e-vaping devices 10 and/or 110 and the corresponding slots 205 and/or 210 based on the generated resistance.

According to at least one example embodiment, and for purposes of detecting the above-described physical connection(s) and/or generating the above-described resistance, the interfaces 266 and 268 may operate as set forth in U.S. patent application Ser. No. 15/067,323, filed Mar. 11, 2016, the entire contents of which are incorporated herein by reference.

According to one or more example embodiments, various types of information regarding the e-vaping device 10, such as remaining charge on the battery of the power supply 145, the remaining amount of pre-vapor formulation in the first section 15, vapor topography data, or the like, may be optically transmitted to the PCC 200 via the LED 170 and the optical sensor 260, thus eliminating a need for an additional, designated pin at the interface 266, 268 or interface 195 for transfer of such information.

Figure 2C:
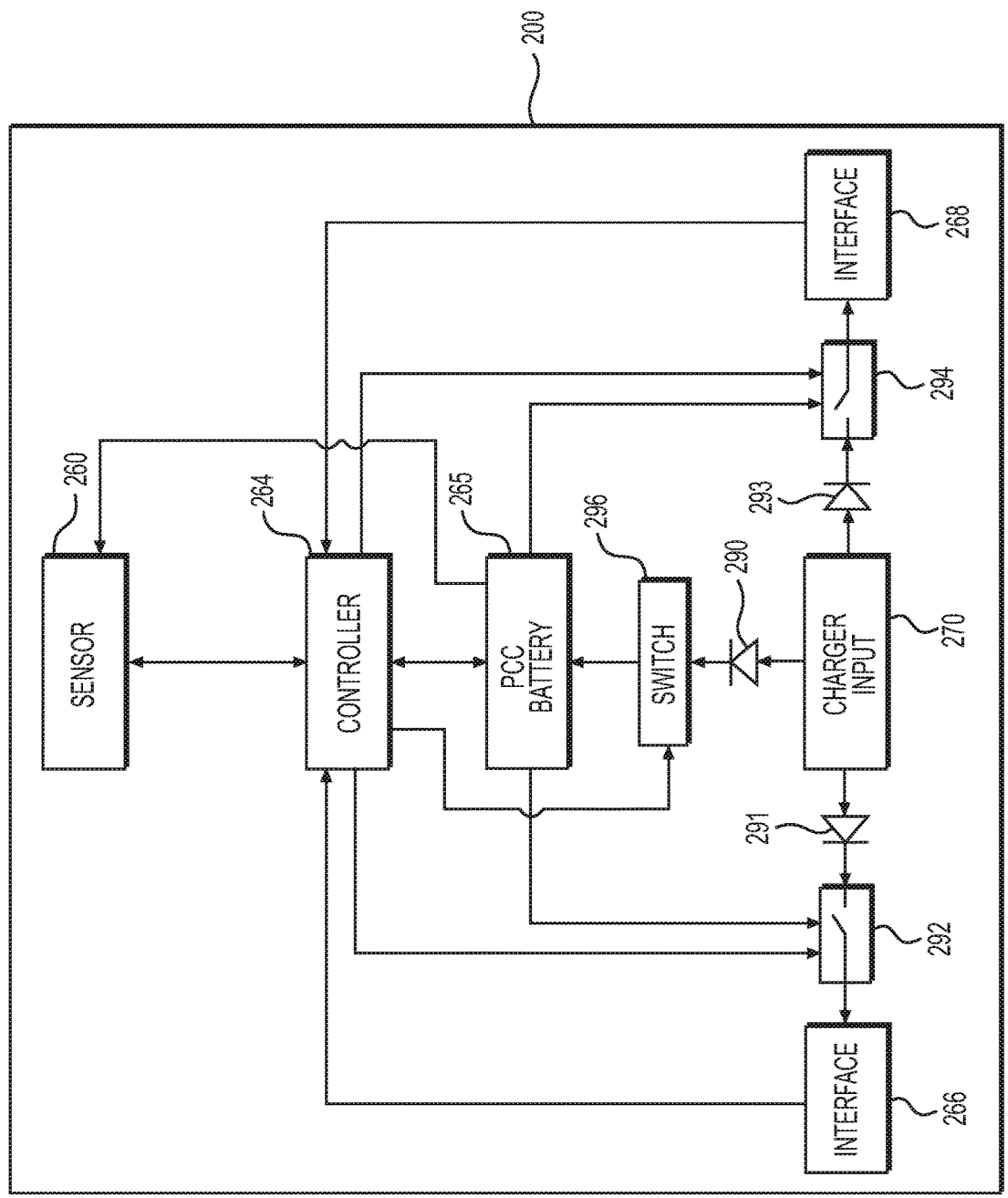
FIG. 2C is a block diagram illustrating example electrical connections between various components of the PCC shown in FIGS. 2A-2B.

FIG. 2C is a diagram of electrical connections among various components of embodiments of the PCC shown in FIGS. 2A-2B, according to one example embodiment. As shown in FIG. 2C, the controller 264 may be connected to the PCC battery 265 and the optical sensor 260. In one example embodiment, the PCC battery 265 provides power to the controller 264 and the optical sensor 260 for operation thereof. However, example embodiments are not limited thereto.

As also shown in FIG. 2C, the charger input 270 may be connected to the PCC battery 265, such that whenever the PCC 200 is connected to an external power source, power may flow from the external power source to the PCC battery 265 via the charger input 270. In at least one example embodiment, there may be a diode such as the diode 290 between the PCC battery 265 and the charger input 270 for ensuring a uni-directional flow of electrical charge from the external power source to the PCC battery 265 and not vice-versa.

The charger input 270 may be connected to the interface 266 via a diode 291 and a switch 292. Similar to the diode 290, the diode 291 ensures a uni-directional flow of electrical charge from the external power source to the interface 266 (e.g., for purposes of charging the power supply 145 of e-vaping device 10 via interface 195 once inserted into slot 205) and not vice-versa. In one example embodiment, the switch 292 may be controlled by the controller 264 to selectively allow power to flow from the PCC battery 265 and/or an external power source to the interface 266. In one example embodiment, the controller 264 may cause the switch 292 to connect to the PCC battery 265 to allow power to flow from the PCC battery 265 to the interface 266, or to the diode 291 to allow power to flow from the external power source to the interface 266.

Similarly, the charger input 270 is connected to the interface 268 via a diode 293 and a switch 294. Similar to the diodes 290 and 291, the diode 293 ensures a uni-directional flow of electrical charge from the external power source to the interface 268 (e.g., for purposes of charging the power supply 145 of the e-vaping device 10 via the interface 195 once inserted into the slot 210) and not vice-versa. In at least one example embodiment, the switch 294 may be controlled by the controller 264 to selectively allow power to flow from the PCC battery 265 or an external power source to the interface 268. In this example, the controller 264 may cause the switch 294 to connect to the PCC battery 265 to allow power to flow from the PCC battery 265 to the interface 268, or to the diode 294 to allow power to flow from the external power source to the interface 268.

The controller 264 is electrically connected to the optical sensor 260 in order to control the operation thereof. In at least one example embodiment, the controller 264 controls the optical sensor 260 by directing the optical sensor 260 to receive encoded information (via light signals) from the LED 170 in response to detecting a triggering event (e.g., upon the e-vaping device 10 being inserted into the PCC 200). In at least one example embodiment, the controller 264 receives electrical signals corresponding to received light signals from the optical sensor 260 via the electrical connection there between.

Figure 3:
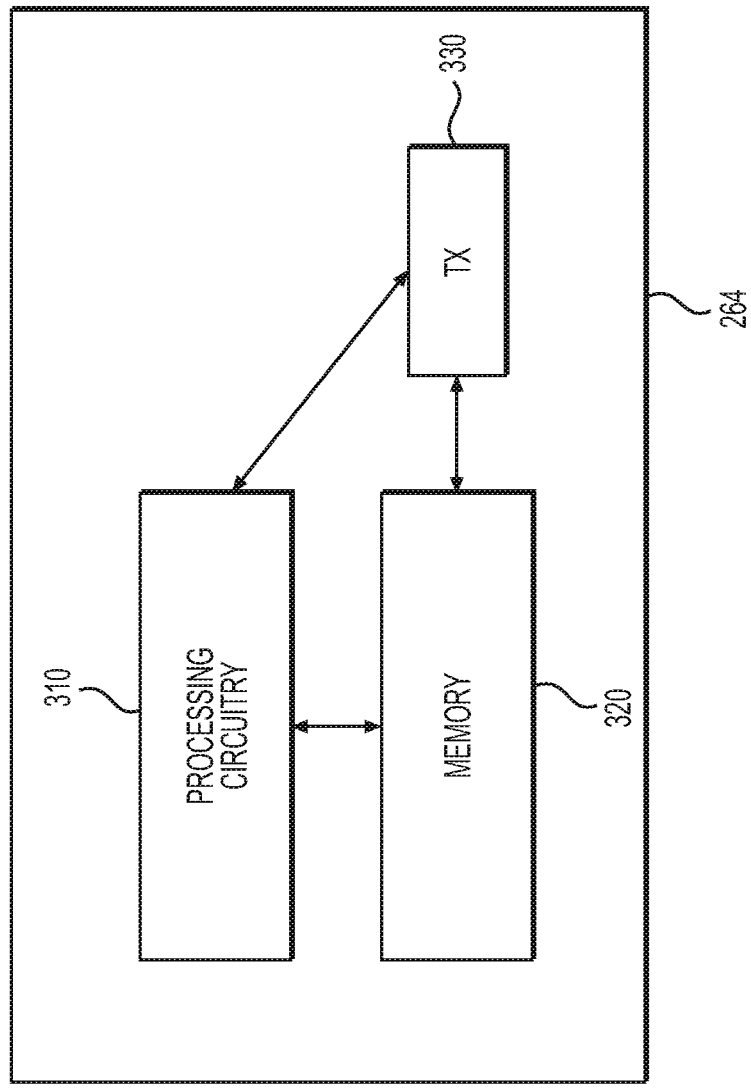
FIG. 3 illustrates an example embodiment of a controller of the PCC shown in FIGS. 2A-2C.

FIG. 3 is a block diagram illustrating an example embodiment of the controller 264 shown in FIG. 2B.

As shown in FIG. 3, the controller 264 includes processing circuitry (e.g., at least one processor) 310, a memory 320, and a transceiver 330. The processing circuitry 310, the memory 320, and the transceiver 330 may be communicatively coupled with one another.

In at least some example embodiments, the transceiver 330 may be any known, or to be developed, transceiver for transmission and/or reception of data, for example and without limitation, between the PCC 200 and a remote device. In at least one example embodiment, the transceiver 300 may enable the establishment of wireless communication between the PCC 200 and a remote device. In another example, the transceiver 300 may enable the establishment of a wired connection with a remote device via the charger input 270 (e.g., via a USB connection or the like).

In at least one example embodiment, the processing circuitry 310 may include at least one processor. In this example, the processor may be any known, or to be developed, processor configured to execute computer-readable instructions stored on the memory 320. Execution of the computer-readable instructions stored on the memory 320 transforms the at least one processor into a special purpose processor for carrying out at least the functionality described herein.

Although discussed in some cases with regard to a processor and a memory, according to at least some example embodiments, the controller 264 (or control circuitry or processing circuitry) may be (or include) hardware, firmware, hardware executing software, or any combination thereof. For example, the controller 264 may include one or more Central Processing Units (CPUs), digital signal processors (DSPs), application-specific-integrated-circuits (ASICs), field programmable gate arrays (FPGAs), or other circuitry configured as special purpose machines to perform the functions of the controller 264.

In at least some example embodiments, the processing circuitry 310 may send appropriate signals/commands to other components of the PCC 200 and/or the e-vaping device 10. For example, the processing circuitry 310 may send a command to optical sensor 260 to activate the optical sensor 260 to receive information (e.g., vapor topography data) in the form of light signals from the e-vaping device 10.

Figure 6:
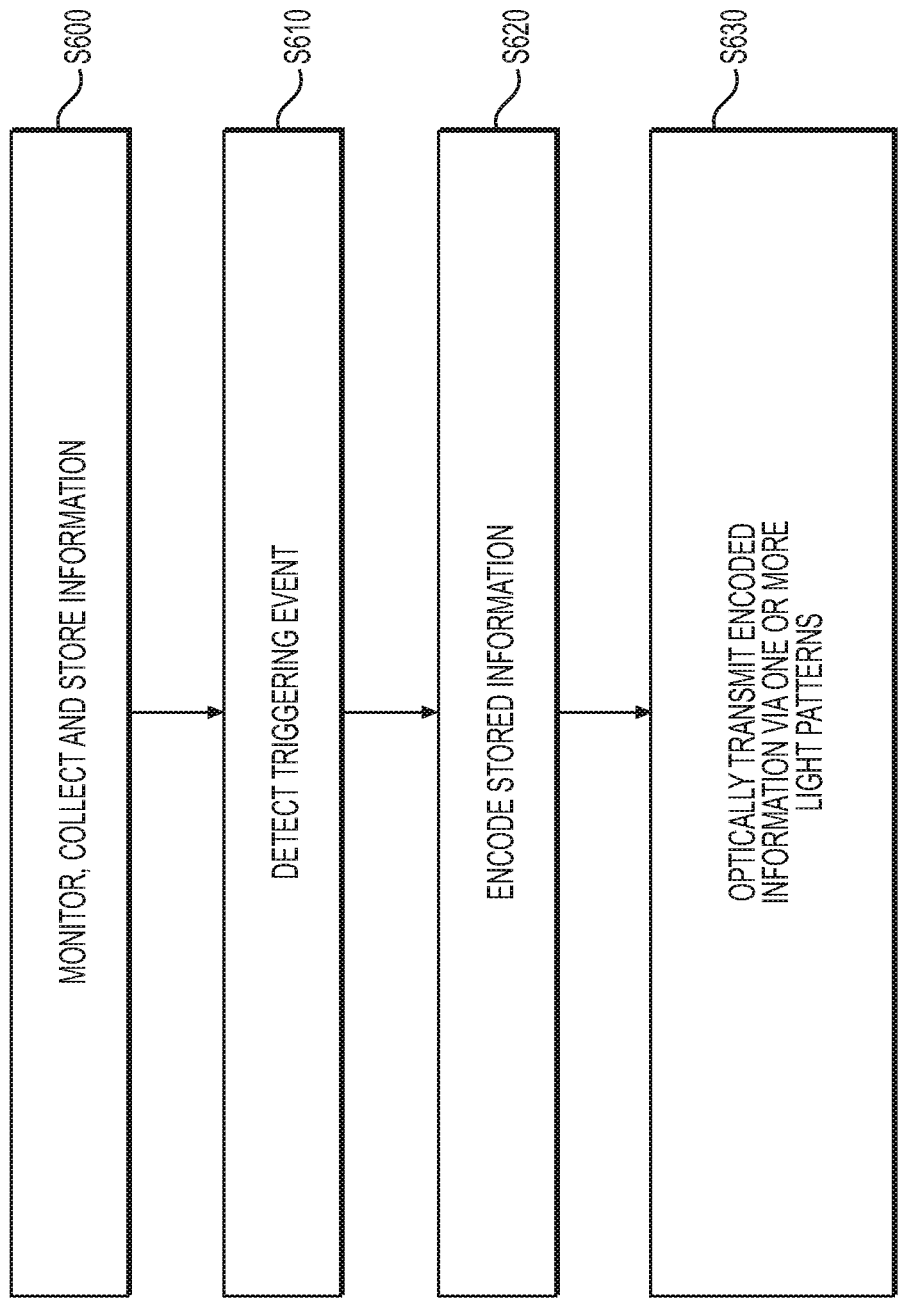
FIG. 6 describes example functionality of a controller of the electronic vaping device embodiments shown in FIGS. 1A-1C, according to an example embodiment.

FIG. 6 is a flow chart illustrating example operation of the controller 185 of an e-vaping device 10, according to an example embodiment. While FIG. 6 will be described from the perspective of a controller 185, it will be understood that in certain example embodiments, the operations shown in FIG. 6 may be performed by processing circuitry 510. Furthermore, FIG. 6 will be described with reference to an e-vaping device 10 being inserted into the slot 205 of a PCC 200 in the process described in FIG. 6. It should be understood, however, that the process shown in FIG. 6 may be applied (e.g., serially, concurrently, and/or simultaneously) with regard to an e-vaping device (e.g., an e-vaping device 110) being inserted into a slot 210 of PCC 200 instead of slot 205.

Referring to FIG. 6, at S600 the controller 185 monitors and collects various types of information regarding the e-vaping device 10. For example, the controller 185 may monitor and collect information including, but not limited to, vapor topography data, an amount of remaining pre-vapor formulation in the first section 15, an amount of remaining charge available on the power supply 145, a number of applications of negative pressure by an adult vaper for the currently connected cartridge, or the like. The controller 185 may monitor and collect such information according to any known or to be developed method. As discussed above, in one example, the controller 185 may monitor and collect vapor topography data generated by a topography apparatus (or by the processor 510) as described above, and further described in, for example, U.S. application Ser. No. 15/604,500, filed May 24, 2017.

In one example, the monitoring and collecting of information may be initiated at power up of the e-vaping device 10. In another example, the monitoring and collecting of information may be initiated by an adult vaper through interaction with the e-vaping device 10, the PCC 200 or an external device communicatively coupled to the e-vaping device 10 or the PCC 200 via a wired or wireless connection. The e-vaping device 10 or the PCC 200 may be communicatively coupled to an electrical device such as a mobile device. The electrical device may send instructions to the e-vaping device 10 or the PCC 200 based on adult vaper input to activate the monitoring and collecting of information. In another example, the controller 185 may initiate monitoring and collecting of information in response to a vapor generation command from the sensor 190.

Also at S600, the controller 185 stores the collected information in the memory 520. The collected information may be stored in the memory 520 in any known manner, such as one or more tables of a database.

Still referring to FIG. 6, upon detecting a triggering event at S610, the controller 185 encodes the stored information at S620.

With regard to S610, according to at least some example embodiments, the triggering event may be the placement of the e-vaping device 10 inside the PCC 200. In this example, the controller 185 may detect a triggering event when the interface 195 contacts, and is electrically connected to, the interface 266 or 268. For example, the controller 185 may detect a triggering event upon receipt of a resistance generated by the circuitry at the interface 195 when the e-vaping device 10 is inserted in, and a physical connection is established with, an interface of the PCC 200.

With regard to S620, in one example, the controller 185 may encode the information using a coding scheme, wherein each type of information is assigned one or more codes, which are then transmitted as light signals by the LED 170. In this example, each code may uniquely identify a given type of information as well as a value thereof. According to at least some example embodiments, any known or to be developed coding scheme for use with transmission of light signals may be used. In another example, the controller 185 may encode the information using a channel access method (e.g., Code-Division Multiple Access (CDMA), optical CDMA (O-CDMA), Frequency Division Multiple Access (FDMA), Time Division Multiple Access (TDMA), Light Fidelity (Li-Fi), or the like, wherein each type of information is assigned a particular code, frequency and/or time for transmission. With regard to at least some of these transmission methods, the controller 185 may utilize a "codebook" for encoding the collected information. The codebook may be stored in the memory 520. In another example, stored information may be encoded using a light pattern by assigning a color, blinking frequency, combination thereof, or the like, to the information. An example coding scheme in which light patterns of color and/or frequency are used is discussed in more detail below.

For example, a continuous red light may be indicative of information corresponding to (may represent) a charge level of less than about 10% inside the power supply 145, a continuous green light may be indicative (represent) of a fully charged power supply 145, and a red light blinking once every 1 millisecond (a blinking frequency of 1 per millisecond) may be indicative of (represent) a charge level between about 10% and about 25% inside the power supply 145. In this example, if the charge level of the power supply 145 is less than about 10%, then the controller 185 may encode the charge level information by converting the charge level into a continuous red light to be transmitted by the LED 170.

Similarly, a green light may be indicative of information corresponding to (may represent) the remaining amount of pre-vapor formulation in the first section 15. For example, a constant green light may be indicative of (represent) about 100% (or an amount above a first threshold value, e.g., about 90%) of the pre-vapor formulation remaining inside the first section 15, a green light blinking once every 1 millisecond (a blinking frequency of 1 per millisecond) may be indicative of (represent) about 50% of the pre-vapor formulation remaining in the first section 15, and a green light blinking twice every 1 millisecond (a blinking frequency of 2 per millisecond) may be indicative of (represent) about 20% of the pre-vapor formulation remaining in the first section 15.

A blue light may be indicative of information corresponding to (may represent) different ranges of number of applications of negative pressure (puffs) associated with the e-vaping device 10. For example, constant blue light (a zero blinking frequency) may be indicative of (represent) a range of about 0-10 for the number of applications of negative pressure (e.g., since the attachment/installment of a new cartridge), a blue light blinking once every 1 millisecond (a blinking frequency of 1 per millisecond) may be indicative of (represent) a range of about 10-20 for the number of applications of negative pressure, and a blue light blinking twice every 1 millisecond (a blinking frequency of 2 per millisecond) may be indicative of (represent) a range of about 20-30 for the number of applications of negative pressure. More generally, a blue light blinking for a number of times about every 1 millisecond may be indicative of (represent) a number of applications of negative pressure that is equal or substantially equal to the number of times the blue light blinks every 1 millisecond.

Returning to FIG. 6, at S630 the controller 185 controls the LED 170 to optically transmit the encoded information to the PCC 200 by emitting one or more light signals and/or patterns of light, which will be received at the PCC 200 by the optical sensor 260.

In one example embodiment, the controller 185 controls the LED 170 to output a different lighting pattern (e.g., a different color, a different blinking frequency and/or a combination thereof as discussed above) for transmission of different types of information to the PCC 200. In another example, the controller 185 may control the LED 170 to output the encoded information using a channel access and/or coding scheme.

While some example embodiments are discussed herein with regard to using different light patterns, coding schemes or channel access methods to convey/transmit various information regarding the e-vaping device 10 using the LED 170, example embodiments are not limited thereto. Rather, any other light pattern, coding scheme, or the like, may be defined/programmed into the controller 185 for transmission of information from the e-vaping device 10 to the PCC 200 via the LED 170 and the optical sensor 260 of the PCC 200. Any other type of color, blinking frequencies, codes (e.g., such as Morse code, binary codes, codes corresponding to 1's and 0's, or the like), combinations of various colors and blinking frequencies, or the like, may be used to optically transmit the collected information to the PCC 200.

In at least one example embodiment, the controller 185 may enable/direct the LED 170 to output a specific lighting pattern through the execution of computer-readable instructions, corresponding to each lighting pattern that is saved on the memory 520 of the controller 185, by the processor 510.

Figure 7:
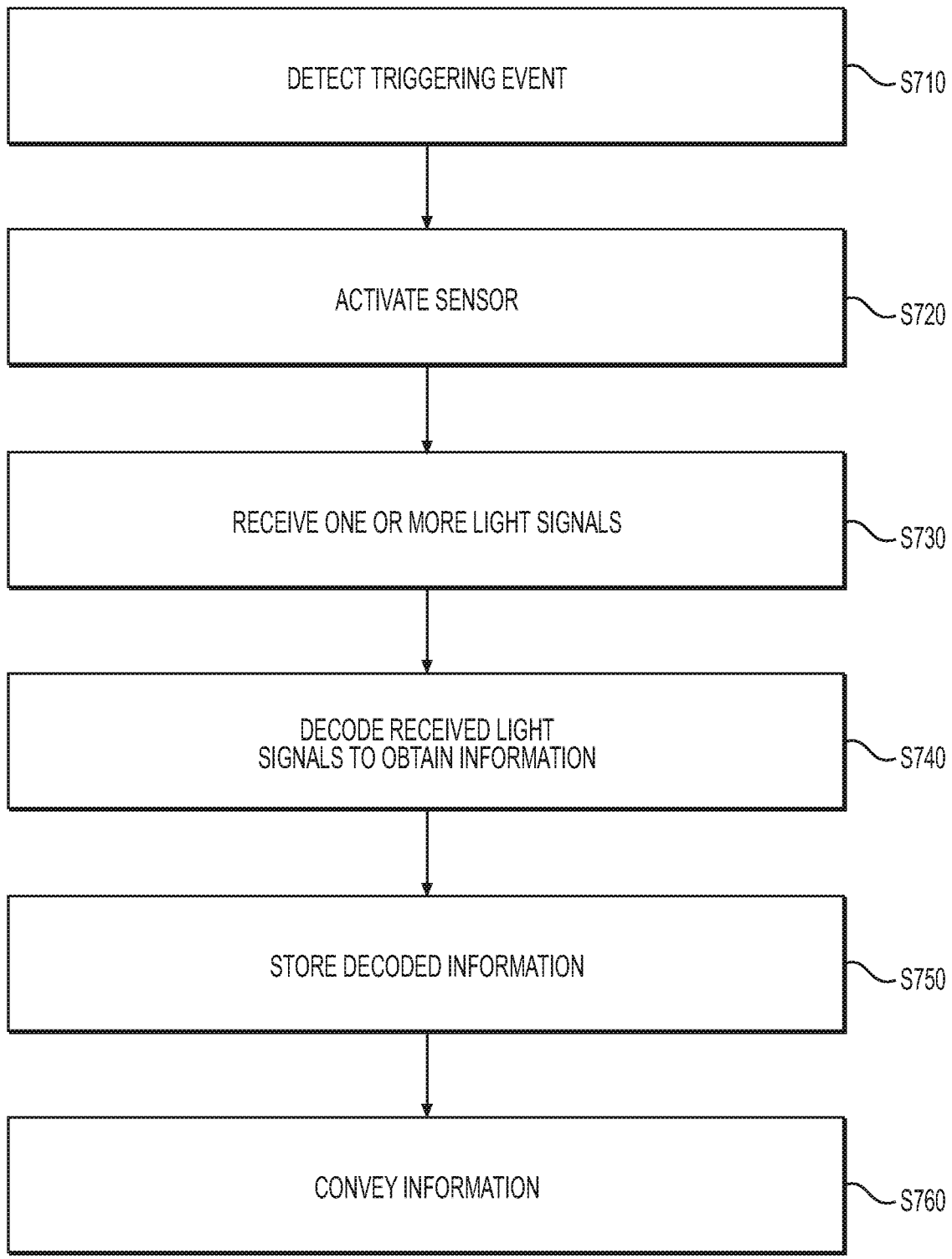
FIG. 7 describes example functionality of a controller of the PCC shown in FIGS. 2A-2C, according to an example embodiment.

FIG. 7 is a flow chart illustrating example operation of a PCC 200 shown in FIGS. 2A-2C, according to an example embodiment.

While FIG. 7 will be described from the perspective of a controller 264, it will be understood that in certain embodiments, each function discussed herein may be performed by processing circuitry 310. Furthermore, FIG. 7 will be described with reference to the e-vaping device 10 being inserted into the slot 205 of the PCC 200 in the process described in FIG. 7. It should be understood, however, that the process shown in FIG. 7 may be applied (e.g., serially, concurrently, and/or simultaneously) with regard to an e-vaping device (e.g., e-vaping device 110) being inserted into a slot 210 of PCC 200 instead of slot 205.

Referring to FIG. 7, upon detecting an optical sensor triggering event at S710, the controller 264 activates the optical sensor 260 for receiving the optical transmission of information from the LED 170 of the e-vaping device 10 (e.g., receiving light signals and/or light patterns) at S720. In at least one example embodiment, the optical sensor triggering event may be electrical connection between the pins of the interface 195 of the e-vaping device 10 and the pins of the interface 266 on the PCC 200. In this example, the controller 264 detects the optical sensor triggering event when the e-vaping device 10 is inserted into the slot 205 of the PCC 200. For example, the controller 264 may detect a triggering event upon receipt of a resistance generated by the circuitry at the interface 266 or 268 when the e-vaping device 10 is inserted in, and a physical connection is established with, the PCC 200.

In another example embodiment, the controller 264 may include a counter (or other timer) that tracks a desired (or, alternatively, predetermined) time period. In this example, the optical sensor triggering event may occur when the time period expires.

In yet another example, the optical sensor triggering event may be establishing visual communication between the LED 170 and the optical sensor 260.

According to at least one other example embodiment, the optical sensor 260 may be always ON and ready to detect optical signals transmitted by the LED 170. In this example, operations S710 and S720 may be omitted.

Returning to FIG. 7, at S730 the controller 264 receives one or more light signals (encoded information) from the LED 170 via the optical sensor 260. In one example, the optical sensor 260 may convert the light signals into electrical signals representing the encoded information, and output the electrical signals to the controller 264. The optical sensor 260 may convert the received light into electrical signals in any known, or to be developed, manner.

At S740, the controller 264 decodes (processes) the encoded information (e.g., electrical signals from the optical sensor 260). In one example embodiment, the controller 264 may have a database including an association between light patterns (e.g., including colors, blinking frequency, codes, or the like) and a different type of information. The database and the corresponding type of information may be the same or substantially the same as that used by the controller 185 of the e-vaping device 10 for encoding the information for optical transmission. The controller 264 may decode the encoded information (light patterns or electrical signals indicative of the light patterns) by comparing the received light pattern to a plurality of light patterns stored in the database.

For example, the database may include a correspondence between a continuous red light (as one type of light pattern) and a charge level of less than about 10% of the battery inside the power supply 145. Accordingly, upon receiving a continuous red light pattern, the controller 264 decodes the received continuous red light pattern as an indication that the remaining charge on the battery of the power supply 145 is less than about 10%.

Similarly, the database may include a correspondence between a continuous green light (as one type of light pattern) and a remaining amount of pre-vapor formulation of 100% in the first section 15. Accordingly, upon receiving a continuous green light pattern, the controller 264 decodes the received continuous green light pattern as an indication that the remaining amount of pre-vapor formulation in the first section 15 is 100%.

Similarly, the database may include a correspondence between a continuous blue light (as one type of light pattern) and a range of 0-10 for the number of applications of negative pressure associated with the e-vaping device 10. Accordingly, upon receiving a continuous blue light, the controller 264 decodes the received continuous blue light pattern as an indication that the number of applications of negative pressure is between 0 and 10.

Accordingly, the controllers 185 and 264 may be programmed such that each utilizes the same type of light pattern to convey/transmit (or decode) the same type of information.

In another example, the controller 264 may have a codebook for decoding a signal encoded according to a given coding scheme or channel access method. The codebook may correspond to the codebook used to encode the information at the controller 185.

In another example, the controller 264 may decode received binary patterns into any kind of information, including graphics and/or sounds, which the controller 264 may then convey through a display 250 or speaker 251 (e.g., at S760 further described below).

Returning to FIG. 7, at S750 the controller 264 may store the decoded information in the memory 320. In one example, the decoded information may be stored in one or more tables of a database in the memory 320.

At S760, the controller 264 outputs the stored information. In one example, the controller 264 may control the display 250 and/or the speaker 251 to display/output the decoded information. For example, if the decoded information indicates that the charge level of the power supply 145 is less than about 10%, then the controller 264 may display a red light on the display 250 to convey the same to an adult vaper. Alternatively, the controller 264 may control the speaker 251 to produce a warning sound indicating the relatively low charge level of the power supply 145. As another example, if the decoded information indicates that the number of applications of negative pressure are between about 20 and 30, then the controller 264 may control the display 250 to display the same. Aside from these examples, any other type of visual and/or audio indications may be produced and conveyed to an adult vaper regarding the e-vaping device 10, via the display 250 and/or the speaker 251.

According to at least one other example embodiment, the controller 264 may output (e.g., directly output) the decoded information after S740, without necessarily storing the information. In this example, S750 in FIG. 7 may be omitted.

The controller 264 may output the stored information (or directly output the information) on demand; for example, in response to interaction of the PCC 200 with an adult vaper.

In yet another example embodiment, the controller 264 may output the stored information to an external device (e.g., a computer or other electronic device) via a wired or wireless connection. In one example, the controller 264 may detect connection of the PCC 200 to an external device via the charger input 270, and output the stored information to the external device in response to the detected connection.

As mentioned above, optical transmission of data monitored and collected at the e-vaping device 10 to the PCC 200 enables omission of a separate physical connection between the e-vaping device 10 and the PCC 200 (or other external device). For example, a pin to transfer the data from the e-vaping device 10 to the PCC 200, upon placement of the e-vaping device 10 inside the PCC 200, is not necessary by virtue of the optical transmission of the data from the e-vaping device 10 to the PCC 200 using the LED 170 and the optical sensor 260.

While example embodiments are capable of various modifications and alternative forms, embodiments thereof are shown by way of example in the drawings and described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer, or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, or the like may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

As discussed herein, the term "or" should not be interpreted as "exclusive or" or XOR, but may be inclusive of "and/or."

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. An apparatus comprising:
   a first slot configured to receive a first electronic vaping device;
   an optical sensor arranged in the first slot, the optical sensor configured to receive light signals from the first electronic vaping device, the light signals indicative of information associated with the first electronic vaping device; and
   processing circuitry configured to
      initiate the optical sensor to receive the light signals in response to a triggering event, wherein the triggering event is expiration of a timer,
      process the light signals to obtain the information associated with the first electronic vaping device, and
      generate an output based on the information associated with the first electronic vaping device.

2. The apparatus of claim 1, wherein the light signals include a light pattern representing the information associated with the first electronic vaping device.

3. The apparatus of claim 2, further comprising:
a memory storing a plurality of light patterns; wherein
the processing circuitry is configured to decode the light pattern by comparing the light pattern to the plurality of light patterns stored in the memory.

4. The apparatus of claim 3, wherein each of the plurality of light patterns is a combination of one of a plurality of light colors emitted at one of a plurality of frequencies.

5. The apparatus of claim 4, wherein each combination of one of the plurality of light colors and one of the plurality of frequencies corresponds to one type of information associated with the first electronic vaping device.

6. The apparatus of claim 1, wherein the processing circuitry is further configured to decode the light signals to obtain the information associated with the first electronic vaping device.

7. The apparatus of claim 6, further comprising:
a memory storing a codebook, and coupled to the processing circuitry, wherein
the processing circuitry is further configured to decode the light signals according to the codebook.

8. The apparatus of claim 1, wherein the output indicates a status of the first electronic vaping device.

9. The apparatus of claim 1, further comprising:
a memory coupled to the processing circuitry; wherein
the processing circuitry is configured to store the information in the memory.

10. The apparatus of claim 1, wherein the triggering event further comprises placement of the first electronic vaping device within the first slot.

11. The apparatus of claim 1, wherein the triggering event further comprises contacting the first electronic vaping device with the apparatus.

12. The apparatus of claim 1, wherein the triggering event further comprises establishing visual communication between the optical sensor and a light emitting device of the first electronic vaping device.

13. The apparatus of claim 1, wherein the information includes at least one of
a number of applications of negative pressure to the first electronic vaping device,
a charge status of a battery of the first electronic vaping device,
an identification of the first electronic vaping device, or
a status of remaining pre-vapor formulation in a cartridge of the first electronic vaping device.

14. The apparatus of claim 1, further comprising:
a display coupled to the processing circuitry, the processing circuitry further configured to drive the display to display the information.

15. The apparatus of claim 1, further comprising:
an audio output coupled to the processing circuitry, the processing circuitry further configured to drive the audio output to output audio signals indicative of the information.

16. The apparatus of claim 1, further comprising:
a first battery; and
a charger input to connect the apparatus to an external power source, wherein
the processing circuitry is further configured to enable a charging of a battery of the first electronic vaping device via at least one of the first battery or the external power source.

17. An apparatus comprising:
a first slot configured to receive a first electronic vaping device;
an optical sensor arranged in the first slot, the optical sensor configured to receive light signals from the first electronic vaping device, the light signals indicative of information associated with the first electronic vaping device, and the light signals representing a binary code; and
processing circuitry configured to
initiate the optical sensor to receive the light signals in response to a triggering event, wherein the triggering event is expiration of a timer,
decode the binary code to obtain the information associated with the first electronic vaping device, and
generate an output based on the information associated with the first electronic vaping device.

18. An apparatus comprising:
a first slot configured to receive a first electronic vaping device;
an optical sensor arranged in the first slot, the optical sensor configured to receive light signals from the first electronic vaping device, the light signals indicative of information associated with the first electronic vaping device, the information including vapor topography data; and
processing circuitry configured to,
initiate the optical sensor to receive the light signals in response to a triggering event, wherein the triggering event is expiration of a timer,
process the light signals to obtain the information associated with the first electronic vaping device, and
generate an output based on the information associated with the first electronic vaping device.

19. An apparatus comprising:
a first slot configured to receive a first electronic vaping device;
an optical sensor arranged in the first slot, the optical sensor configured to receive light signals from the first electronic vaping device, the light signals indicative of information associated with the first electronic vaping device; and
processing circuitry configured to,
initiate the optical sensor to receive the light singals in response to a triggering event, wherein the triggering event is expiration of a timer,
process the light signals to obtain the information associated with the first electronic vaping device, and
generate an output based on the information associated with the first electronic vaping device;
a body including the first slot; and
a cover element having at least one hollow section corresponding to at least the first slot, the at least one hollow section configured to receive a portion of the first electronic vaping device that extends out of the first slot when inserted therein, the cover element being configured to be opened and closed, the cover element covering the body when closed.

20. An apparatus comprising:
a first slot configured to receive a first electronic vaping device;
an optical sensor arranged in the first slot, the optical sensor configured to receive light signals from the first electronic vaping device, the light signals indicative of information associated with the first electronic vaping device; and processing circuitry configured to,
  process the light signals to obtain the information associated with the first electronic vaping device, and
  generate an output based on the information associated with the first electronic vaping device;
a second slot configured to receive a second electronic vaping device; and
a divider configured to separate the first slot from the second slot, the optical sensor and the processing circuitry positioned on the divider.

21. The apparatus of claim 20, wherein the light signals include a light pattern representing the information associated with the first electronic vaping device.

22. The apparatus of claim 21, further comprising:
a memory storing a plurality of light patterns; wherein
  the processing circuitry is configured to decode the light pattern by comparing the light pattern to the plurality of light patterns stored in the memory.

23. The apparatus of claim 22, wherein each of the plurality of light patterns is a combination of one of a plurality of light colors emitted at one of a plurality of frequencies.

24. The apparatus of claim 23, wherein each combination of one of the plurality of light colors and one of the plurality of frequencies corresponds to one type of information associated with the first electronic vaping device.

25. The apparatus of claim 20, wherein the output indicates a status of the first electronic vaping device.

26. The apparatus of claim 20, further comprising:
a memory coupled to the processing circuitry; wherein
  the processing circuitry is configured to store the information in the memory.

27. The apparatus of claim 20, wherein the processing circuitry is further configured to decode the light signals to obtain the information associated with the first electronic vaping device.

28. The apparatus of claim 20, wherein the processing circuitry is further configured to initiate operation of the optical sensor in response to a triggering event.

29. The apparatus of claim 28, wherein the triggering event is expiration of a timer.

30. The apparatus of claim 28, wherein the triggering event is placement of the first electronic vaping device within the first slot.

31. The apparatus of claim 28, wherein the triggering event is contacting the first electronic vaping device with the apparatus.

32. The apparatus of claim 28, wherein the triggering event is establishing visual communication between the optical sensor and a light emitting device of the first electronic vaping device.

33. The apparatus of claim 20, further comprising:
a display coupled to the processing circuitry, the processing circuitry further configured to drive the display to display the information.

34. The apparatus of claim 20, further comprising:
an audio output coupled to the processing circuitry, the processing circuitry further configured to drive the audio output to output audio signals indicative of the information.

35. The apparatus of claim 20, further comprising:
a first battery; and
a charger input to connect the apparatus to an external power source, wherein
  the processing circuitry is further configured to enable a charging of a battery of the first electronic vaping device via at least one of the first battery or the external power source.

36. The apparatus of claim 20, wherein the information includes at least one of
  a number of applications of negative pressure to the first electronic vaping device,
  a charge status of a battery of the first electronic vaping device,
  an identification of the first electronic vaping device, or
  a status of remaining pre-vapor formulation in a cartridge of the first electronic vaping device.

* * * * *